US00PP37680P2

(12) United States Plant Patent
Danziger

(10) Patent No.: US PP37,680 P2
(45) Date of Patent: Sep. 8, 2026

(54) ***GAILLARDIA* PLANT NAMED 'DGAIGSORZT'**

(50) Latin Name: *Gaillardia aristata*
Varietal Denomination: DGAIGSORZT

(71) Applicant: Danziger "DAN" Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 19/448,528

(22) Filed: Jan. 14, 2026

(51) Int. Cl.
*A01H 6/14* (2018.01)
*A01H 5/02* (2018.01)

(52) U.S. Cl.
USPC ..... Plt./431

(58) Field of Classification Search
USPC ..... Plt./431
CPC ..... A01H 6/14; A01H 5/02
See application file for complete search history.

*Primary Examiner* — Keith O. Robinson

(57) ABSTRACT

A new and distinct cultivar of *Gaillardia* plant named 'DGAIGSORZT' is disclosed, characterized by bright orange flowers on compact plants with an evenly round shape. Plants flower abundantly and begin flowering early. The new variety is a *Gaillardia* typically produced as an ornamental plant.

2 Drawing Sheets

Figure 1:
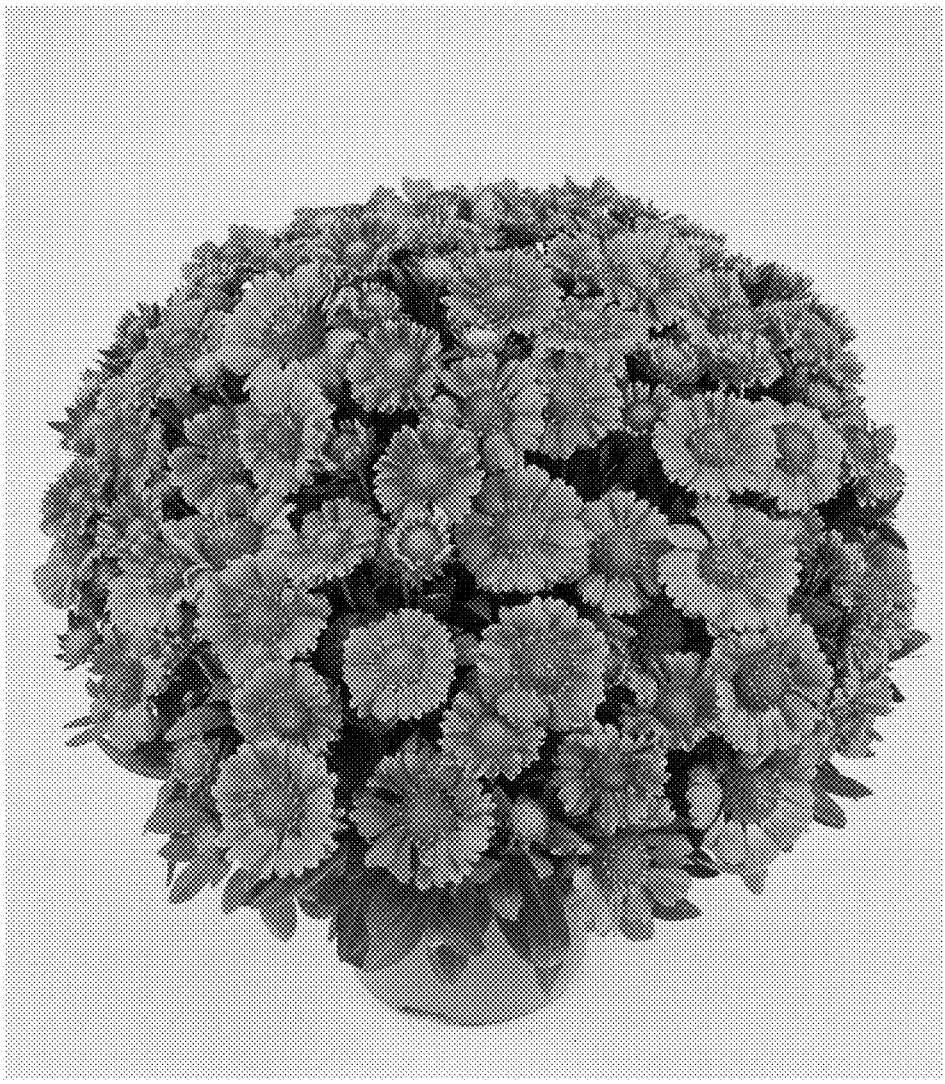

Latin name of the genus and species: *Gaillardia aristata.*
Cultivar denomination: 'DGAIGSORZT'.

BACKGROUND OF THE INVENTION

The new *Gaillardia* cultivar is a product of a planned breeding program conducted by the inventor, Gavriel Danziger in Moshav Mishmar Hashiva, Israel. The objective of the breeding program was to produce new *Gaillardia* varieties for ornamental purposes. The seed parent is an unnamed, unpatented internal *Gaillardia* selection. The pollen parent unidentified as the new cultivar is the result of an open pollination. The open pollination. resulting in this new cultivar was made during May 2021.

The new cultivar was found and selected May 31, 2022 by the inventor in a group of seedlings resulting from the crossing at the same nursery in Moshav Mishmar Hashiva, Israel.

Asexual reproduction of the new cultivar 'DGAIGSORZT' was first performed by terminal vegetative cuttings May 31, 2022, in Moshav Mishmar Hashiva, Israel. Subsequent propagation by vegetative cuttings has shown that the unique features of this cultivar are stable and reproduced true to type in successive generations.

SUMMARY OF THE INVENTION

The cultivar 'DGAIGSORZT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGAIGSORZT'. These characteristics in combination distinguish 'DGAIGSORZT' as a new and distinct *Gaillardia* cultivar:

1. Compact plant with an evenly round shape.
2. Abundant flowering.

3. Early blooming.
4. Bright orange flowers.

PARENT COMPARISON

Plants of the new cultivar 'DGAIGSORZT' are similar to the seed parent in most horticultural characteristics; however, 'DGAIGSORZT' differs in the following:

1. Plants of the new cultivar are more compact than plants of the seed parent.
2. Plants of the new cultivar produce more flowers than plants of the seed parent.
3. Plants of the new cultivar begin flowering 5 to 8 days earlier than plants of the seed parent.

The pollen parent cannot be identified for comparison.

COMMERCIAL COMPARISONS

Plants of the new cultivar 'DGAIGSORZT' can be compared to the commercial cultivar *Gaillardia* 'Gusto Paprika', unpatented. These varieties are similar in most horticultural characteristics; however, 'DGAIGSORZT' differs in the following:

1. Plants of the new cultivar begin flowering 10 to 14 days earlier than plants of this comparator.
2. Plants of the new cultivar are more compact than plants of this comparator.
3. Plants of the new cultivar produce more inflorescences per plant than plants of this comparator.
4. Flower color of the new cultivar is bright orange, while the flower color of this comparator is dusky red.

Plants of the new cultivar 'DGAIGSORZT' can also be compared to the commercial cultivar *Gaillardia* 'Gusto Lemon', unpatented. These varieties are similar in most horticultural characteristics; however, 'DGAIGSORZT' differs in the following:

1. Plants of the new cultivar begin flowering 7 to 10 days earlier than plants of this comparator.

2. Plants of the new cultivar have shorter peduncles by about 20 o 30% than plants of this comparator.
3. Flower color of the new cultivar is bright orange, while the flower color of this comparator is yellow.

BRIEF DESCRIPTION OF THE PHOTOGRAPHS

The accompanying photograph in FIG. 1 illustrates in full color a typical plant of 'DGAIGSORZT' grown in a 20 cm pot in Moshav Mishmar Hashiva, Israel. The plant was 20 weeks of age.

Figure 2:
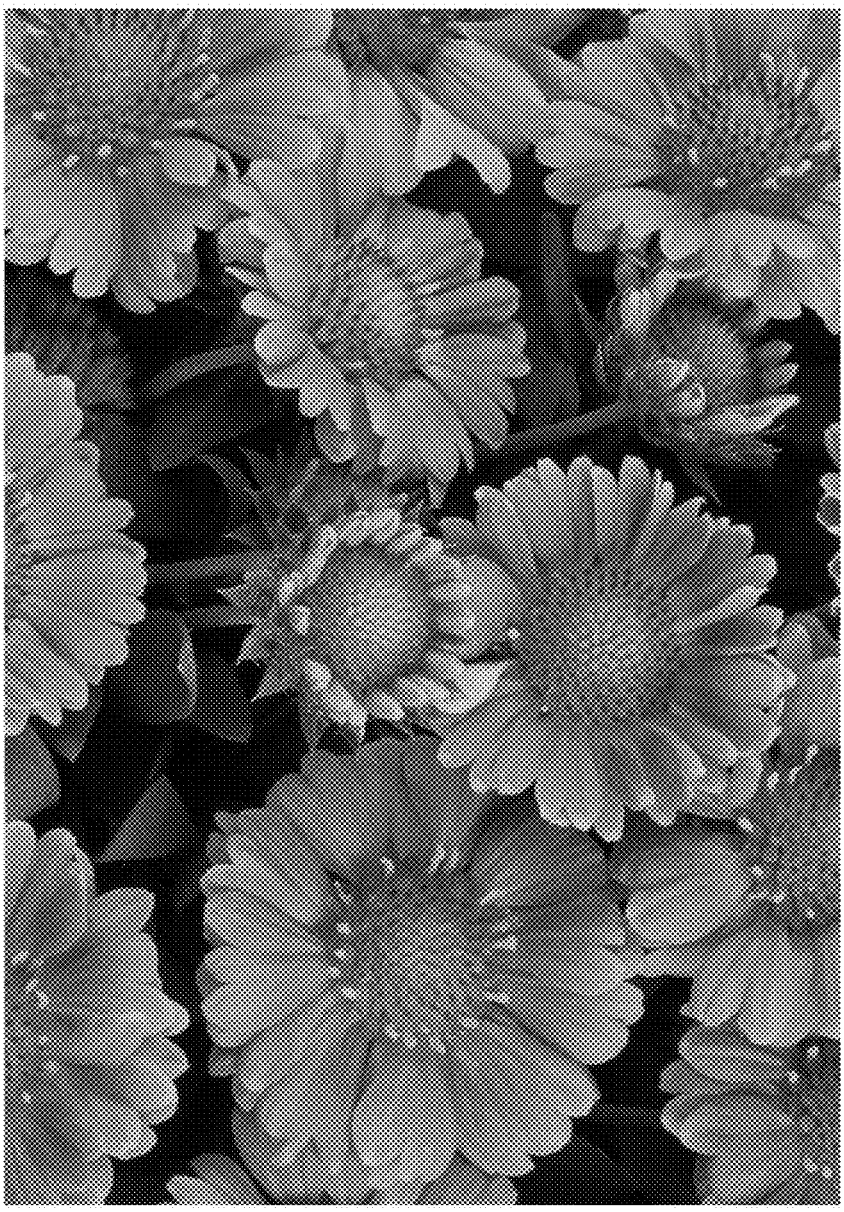

FIG. 2 illustrates in full color a close-up view of typical inflorescences of 'DGAIGSORZT'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DGAIGSORZT' plants grown outdoors in Moshav Mishmar Hashiva, Israel, under natural lighting. Measurements were taken during autumn. The plants were approximately 72 days old from a rooted cutting in a 20 cm pot. The growing temperature ranged from approximately 23° C. to 34° C. during the day, 14° C. to 23° C. during the night. Measurements and numerical values represent averages of typical plant types.

Botanical classification: *Gaillardia aristata* 'DGAIGSORZT'.

PROPAGATION

Total rooting time: 5 to 10 days at approximately 21° C.

Root description: Fine and fibrous. Brown to tan in color, not accurately measured with R.H.S. chart.

PLANT

Plant type: Herbaceous flowering perennial.

Age of plant described: 72 days from a rooted cutting.

Pot size of plant described: 20 cm.

Plant habit: Compact and evenly rounded.

Height: About 24 cm.

Plant spread: About 35 cm.

Growth rate: Moderate to fast, finishing a 20 cm pot in about 10 weeks.

Characteristics of primary branches:

*Diameter.*—Average 4 to 6 mm.

*Color.*—RHS Yellow-Green 144C.

*Texture.*—Slightly pubescent to pubescent.

*Strength.*—Moderately strong, not easily broken during transport or environmental stress.

FOLIAGE

Leaf:

*Attachment.*—Sessile.

*Shape of blade.*—Oblanceolate.

*Quantity.*—Approximately 35 per lateral branch.

*Average Length.*—5.5 cm.

*Average width.*—1.6 cm.

*Apex.*—Acute.

*Base.*—Truncate.

*Margin.*—Entire.

*Texture of top surface.*—Pubescent.

*Texture of bottom surface.*—Pubescent.

*Appearance of top surface.*—Matte.

*Appearance of bottom surface.*—Matte.

*Color.*—Young foliage upper side: Yellow-Green 146C. Young foliage under side: Yellow-Green 146C. Mature foliage upper side: Yellow-Green 146B. Mature foliage under side: Yellow-Green 146B.

*Venation.*—Type: Pinnate. Venation color upper side: Yellow-Green 144A. Venation color under side: Yellow-Green 144A.

Petiole: Absent.

FLOWER

Bloom period: Spring until Fall.

Time to flowering from rooted cutting: About 3 to 5 weeks.

Inflorescence and flower type and habit: Terminal composite inflorescence. Single.

Rate of flower opening: Approximately 3 to 5 days from bud to fully opened flower.

Flower longevity on plant: About 4 to 6 days before any significant change is observed.

Quantity of inflorescences per lateral stem: Average of 5.

Quantity of open inflorescences and buds per plant: About 80.

Persistence: Self-cleaning.

Inflorescence bud:

*Shape.*—Flattened sphere.

*Length.*—Approximately 1 cm.

*Diameter.*—Approximately 1.5 cm.

*Color.*—RHS Yellow-Green 145B.

Inflorescence:

*Diameter.*—Approximately 6.5 cm.

*Depth.*—Approximately 2.4 cm.

*Disc diameter.*—Approximately 3.2 cm.

*Receptacle shape.*—Conical.

*Receptacle height.*—Average 15 mm.

*Receptacle diameter.*—2 cm.

*Receptacle color.*—Near RHS Yellow-Green 144A.

Individual flower bud:

*Shape.*—Broad conical.

*Length.*—Approximately 2 cm.

*Diameter.*—Approximately 1.5 cm.

*Color.*—Main color near RHS Green 137A, turning Yellow 12A towards apex.

Ray florets:

*Quantity.*—25.

*Arrangement.*—Radiate.

*Length.*—2.3 cm.

*Width.*—1.4 cm.

*Shape.*—Narrow cordate.

*Apex.*—2 obtuse lobes.

*Base.*—Acuminate.

*Margin.*—Entire.

*Texture, upper and lower surfaces.*—Smooth, glabrous.

*Color.*—When opening, upper surface: 26A. Apex 17B. When opening, lower surface: 22A. Apex 17B. Fully opened, upper surface: N25C. Apex 14B. Fully opened, lower surface: 22A. Apex 14B.

Disc florets:
*Quantity*.—Average 140.
*Arrangement*.—Spirally.
*Length*.—8 mm.
*Width*.—2 mm.
*Shape*.—Tubular.
*Apex*.—Emarginate.
*Base*.—Fused.
*Margin*.—Entire.
*Texture, upper and lower surfaces*.—Pubescent.
*Color*.—When opening, towards apex: 15C. When opening, towards base: 15C. Fully opened, towards apex: N30C. Fully opened, towards base: 15C.

Fragrance: Light, sweet scent.

Phyllaries/involucral bracts:
*Quantity per inflorescence*.—Average 25, in 3 whorls.
*Shape*.—Narrow ovate to lanceolate.
*Length*.—Average range 15 mm to 40 mm. Interior whorl are shortest.
*Width*.—Average range 3 mm to 15 mm. Interior whorl are narrowest.
*Apex*.—Acute.
*Base*.—Truncate.
*Margin*.—Entire with short pubescence.
*Texture*.—Upper and lower surfaces lightly pubescent.
*Color*.—Upper Surface: RHS Yellow-Green 147B. Lower Surface: RHS Yellow-Green 147B.

Peduncle:
*Length*.—Average 7.5 cm.
*Diameter*.—Approximately 3 mm.
*Texture*.—Lightly pubescent.
*Color*.—RHS Yellow-Green 146C.

REPRODUCTIVE ORGANS

Ray florets:

Androecium: Absent.

Gynoecium: Absent.

Disc florets:

Androecium:

Stamens:
*Number*.—5.
*Filament length*.—Approximately 2 mm.

Anthers:
*Length*.—Approximately 1 mm.
*Shape*.—Linear.
*Color*.—17A.
*Pollen*.—Abundant, colored near 17B.

Pistil:
*Number*.—1.
*Length*.—Approximately 6 mm.
*Style*.—Length: Approximately 5 mm. Color: 13B.
*Stigma*.—Shape: Two lobed. Color: 13B. Ovary size: About 3 mm by 3 mm. Ovary color: 6D.

OTHER CHARACTERISTICS

Disease resistance: Neither resistance nor susceptibility to additional normal diseases and pests of *Gaillardia* has been observed.

Seed production: About 30 seeds per inflorescence.
*Shape*.—Oblong.
*Color*.—Grey-Brown N199B.
*Size*.—Approximately 3 mm long and 2 mm wide.

What is claimed is:

1. A new and distinct cultivar of *Gaillardia* plant named 'DGAIGSORZT' as herein illustrated and described.

* * * * *